(12) United States Patent
Mewshaw et al.

(10) Patent No.: US 6,489,342 B2
(45) Date of Patent: Dec. 3, 2002

(54) ARYLOXY PIPERIDINYL INDOLES FOR TREATING DEPRESSION

(75) Inventors: Richard E. Mewshaw, King of Prussia, PA (US); Dahui Zhou, East Brunswick, NJ (US); Ping Zhou, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/002,340

(22) Filed: Nov. 15, 2001

(65) Prior Publication Data

US 2002/0099078 A1 Jul. 25, 2002

Related U.S. Application Data

(60) Provisional application No. 60/249,633, filed on Nov. 17, 2000.

(51) Int. Cl.[7] .................. A61K 31/454; A61K 31/4439; C07D 401/14
(52) U.S. Cl. .................. 514/323; 514/339; 540/201; 540/277.4; 540/278.1
(58) Field of Search .............................. 546/201, 277.4, 546/278.1; 514/323, 339

(56) References Cited

U.S. PATENT DOCUMENTS 5,114,949 A    5/1992  Gueremy et al.

FOREIGN PATENT DOCUMENTS

| EP | 0 714 894 A1 | 6/1996 |
|---|---|---|
| EP | 0 722 941 A2 | 7/1996 |
| WO | WO 96/26923 | 9/1996 |

OTHER PUBLICATIONS

Mignani et al., New Indole Derivatives as Potent and Selective Serotonin Uptake Inhibitors, Bioorganic & Medicinal Chemistry Letters, 1993, vol. 3, No. 10, pp 1913–1918, Pergamon Press Ltd, Great Britain.

Malleron et al., New Indole Derivatives as Potent and Selective Serotonin Uptake Inhibitors, J. Med. Chem. 1993, 36, 1194–1202.

*Primary Examiner*—Patricia L. Morris
(74) *Attorney, Agent, or Firm*—Joseph M. Mazzarese

(57) ABSTRACT

This invention provides aryloxy indole derivatives which are useful for the treatment of diseases affected by disorders of the serotonin-affected neurological systems, such as depression and anxiety, the compounds having the formula:

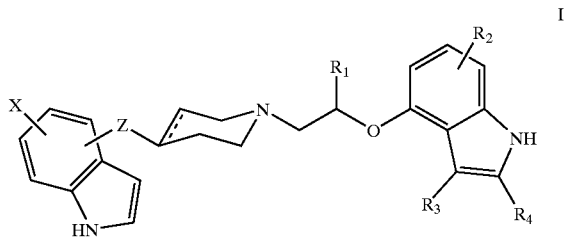

wherein $R_1$ is H or alkyl; $R_2$, $R_3$, and $R_4$ are H, alkyl, or halogen; X is H, halogen, CN, or $C_1$–$C_6$ alkoxy; Z is $(CH_2)_n$ or carbonyl; n is 1 or 2; and the dashed line indicates an optional double bond; or a pharmaceutically acceptable salt thereof.

10 Claims, No Drawings

ARYLOXY PIPERIDINYL INDOLES FOR TREATING DEPRESSION

This application claims priority from provisional application Ser. No. 60/249,633 filed Nov. 17, 2000, abandoned, the entire disclosure of which is hereby incorporated by reference.

This invention relates to new aryloxy indole derivatives as pharmaceuticals which are useful for the treatment in mammals of diseases affected by disorders of the serotonin-affected neurological systems, such as depression, anxiety, panic disorder, obsessive-compulsive disorder, sleep disorders, sexual dysfunction, bipolar disorders, psychosis, stress-related disorders, including post-traumatic stress disorders, Tourettes' syndrome, attention deficit disorder, with and without hyperactivity, alcohol and drug addiction, Alzheimer's disease, Parkinson's disease, obesity and acute and chronic pain, including migraine pain, as well as methods of enhancing cognition.

BACKGROUND OF THE INVENTION

EP 0714894 A1 discloses the preparation of compounds of formula II as new $5\text{-HT}_{1f}$ agonist for the treatment of migraine headaches. EP 429341 A2 claims compounds of formula III as having serotonin transporter activity. A recent publication by Malleron et al. was also reported based around formula I [J. Med. Chem. 36, 1194 (1993)]. EP 722941 A2 discloses compounds having effects on serotonin-related systems of formula IV.

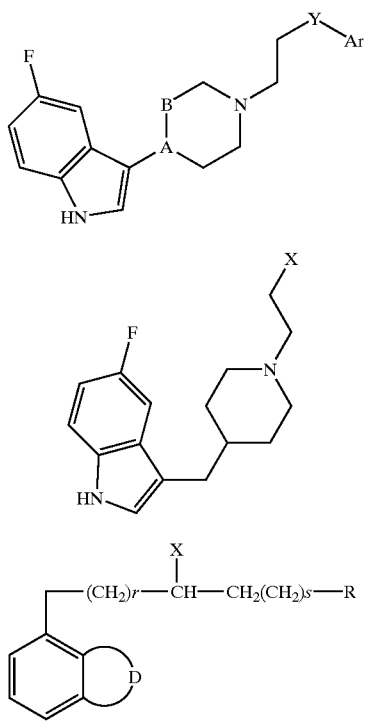

Pharmaceuticals which enhance serotonergic neurotransmission are of useful benefit for the treatment of many psychiatric disorders, including depression and anxiety. The first generation of non-selective serotonin-affecting drugs operated through a variety of physiological functions which endowed them with several side effect liabilities. The more currently prescribed drugs, the selective serotonin (5-HT) reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism per se cannot account for their therapeutic activity. It is speculated that this two week induction which occurs before a full antidepressant effect is observed, is due to the involvement of the $5\text{-HT}_{1A}$ autoreceptors which suppress the firing activity of 5-HT neuron, causing a dampening of the therapeutic effect. Studies suggest that after several weeks of SSRI administration, a desensitization of the 5-HT autoreceptors occurs allowing a full antidepressant effect in most patients. Recent studies by Artigas et al. (Trends Neurosci., 1996, 19, 378–383) suggest a combination of $5\text{-HT}_{1A}$ activity and inhibition of 5-HT uptake within a single molecular entity can achieve a more robust and fast-acting antidepressant effect.

The present invention relates to a new class of molecules which have the ability to act at the $5\text{-HT}_{1A}$ autoreceptors and concomitantly with the 5-HT transporter. Such compounds are therefore potentially useful for the treatment of depression as well as other serotonin disorders.

SUMMARY OF INVENTION

The compounds of this invention are aryloxy piperidinyl indoles represented by Formula I:

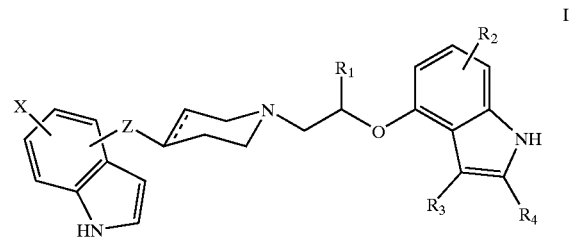

wherein:

$R_1$ is hydrogen or alkyl of from 1 to 6 carbon atoms;

$R_2$, $R_3$, and $R_4$ are each independently selected from hydrogen, alkyl of from 1 to 6 carbon atoms, or halogen;

X is selected from hydrogen, halogen, CN, or $C_1$–$C_6$ alkoxy;

Z is $(CH_2)_n$ or carbonyl;

n is 1 or 2; and the dashed line indicates an optional double bond;

or a pharmaceutically acceptable salt thereof.

One group of compounds of this invention comprises those of the formula:

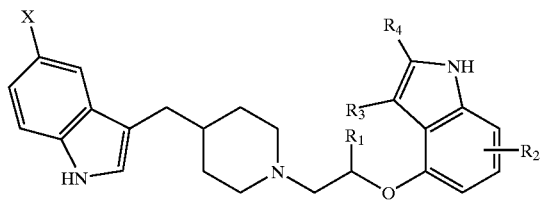

wherein:

X is selected from hydrogen, halogen, CN, or $C_1$–$C_6$ alkoxy;

$R_1$ is hydrogen or alkyl of from 1 to 3 carbon atoms; and $R_2$, $R_3$, and $R_4$ are each independently selected from hydrogen, alkyl of from 1 to 6 carbon atoms, or halogen;

or a pharmaceutically acceptable salt thereof.

Another group of compounds of this invention comprise those of the formula:

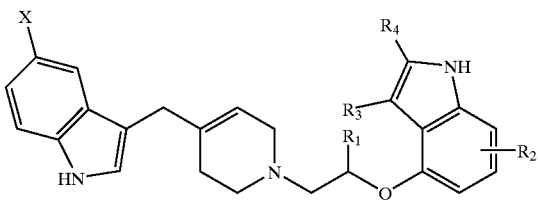

wherein:

X is selected from hydrogen, halogen, CN, or $C_1$–$C_6$ alkoxy;

$R_1$ is hydrogen or alkyl of from 1 to 3 carbon atoms; and $R_2$, $R_3$, and $R_4$ are each independently selected from hydrogen, alkyl of from 1 to 6 carbon atoms, or halogen;

or a pharmaceutically acceptable salt thereof.

The compounds of this Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of Formula I are generally prepared by the overall sequence indicated in Scheme 1 as follows:

Scheme 1

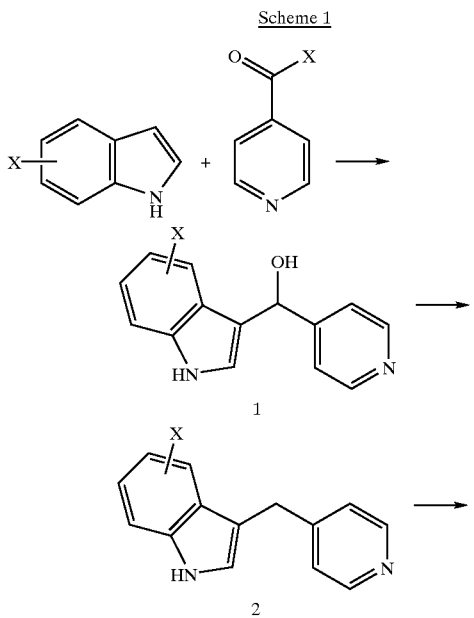

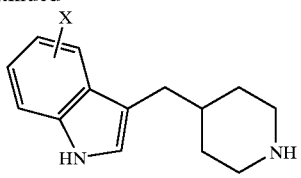

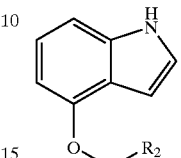

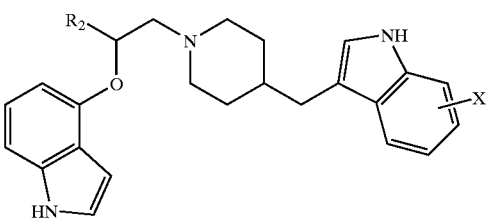

Ex 1,2

The following examples for preparation of intermediates and invention compounds are included for illustrative purposes and are not to be construed as limiting to this disclosure in any way. Those skilled in the art of organic synthesis may be aware of still other synthetic routes to the invention compounds. The reagents and intermediates used herein are either commercially available or prepared according to standard literature procedures.

Intermediate 1

(5-Fluoro-1H-indol-3-yl)-pyridin-4-yl-methanol. To a stirred solution of 5-fluoroindole (3.10 g, 23.0 mmol) in methanol (10.0 mL) was added 4-pyridinecarboxaldehyde (2.20 mL, 23.0 mmol), followed by addition of NaOH (2.5 mL, 50%) at 0° C. After stirring for 1 h at 0° C., the reaction mixture was warmed to room temperature and stirred for 3 h, followed by the addition of water (10.0 mL). The precipitate was collected by filtration and dried under vacuum to afford 5.2 g (93%) of a light yellow solid: mp 171–173° C.; $^1$H NMR (DMSO, 400 MHz), 5.85 (d, 1H), 5.93 (d, 1H), 6.86–7.34 (m, 4H), 7.43 (dd, 2H), 8.48 (dd, 2H), 11.09 (br s, 1H); MS (El) m/z 242 (M$^+$); HRMS calcd for $C_{14}H_{12}FN_2O$ [M+H] 243.09337, found 243.09576.

Intermediate 2

5-Fluoro-3-[(4-pyridinyl)methyl]-1H-indole. To a suspension of (5-fluoro-1H-indol-3-yl)-pyridin-4-yl-methanol (0.799 g, 3.3 mmol) in methylene chloride (13 mL) was added triethylsilane (0.60 mL, 3.7 mmol) followed by trifluoroacetic acid (2.85 mL, 37 mmol) at room temperature. After addition of trifluoroacetic acid, a clear black solution was obtained. The reaction mixture was stirred overnight and the solvent and excess trifluoroacetic acid was removed on a rotary evaporator. To the residue was added saturated Na$_2$CO$_3$ to adjust the pH>9. The aqueous layer was extracted with methylene chloride and the combined organic extracts was washed with water, brine, dried over anhydrous sodium sulfate, filtered, and concentrated. The crude product was purified by silica gel column chromatography (methylene chloride to methylene chloride/ethyl acetate to ethyl acetate, 100% to 50% to 100%) to give 0.56 g (75%) of a solid: mp 141–142° C. [(mp 149° C.; previously reported in J. Med. Chem. 36,1194 (1993)].

Intermediate 3

5-Fluoro-3-[(4-piperidinly)methyl]-1 H-indole. This compound was prepared from intermediate 2 in 88% yield following the reported procedure (Malleron et.al, J. Med. Chem. 1993, 36, 1194).

Intermediate 4a,b (4a) 2-(1H-Indol-4-yloxy)-chloroethane: This compound was prepared from 5-hydroxyindole and chloroethanol in 57% using Mitsunobu conditions as reported in the literature (Mewshaw et al. J. Med. Chem. 1999, 42, 2007); mp 62–63° C.; $^1$H NMR (CDCl$_3$) 3.88 (2H, t, J=6.2 Hz), 4.38 (2H, t, J=6.2 Hz), 6.52 (1H, d, J=7.3 Hz), 6.68 (1H, app. t, J=2.2 Hz), 7.02–7.12 (3H, m), 8.14 (1H, s).

(4b) 2-Methyl-2-(1H-indol-4-yloxy)-chloroethane was similarly prepared as described above as a yellow oil: (47%); MS (EI) 209 (M+).

EXAMPLE 1

5-Fluoro-3-{1-[2-(1H-indol-4-yloxy)ethyl]-piperidin-4-ylmethyl}-1H-indole

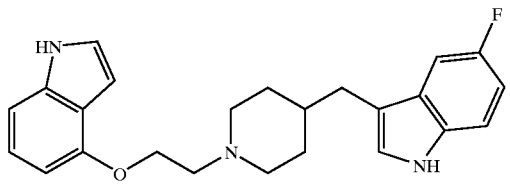

To a solution of 5-fluoro-3-[(4-piperidinyl)methyl]-1H-indole (0.84 g, 3.6 mmol) in acetonitrile (50 mL) was added 4-(2-chloroethoxy)-1H-indole (0.59 g, 3.6 mmol), potassium carbonate (0.48 g) followed by addition of potassium iodide (0.60 g) at room temperature. The reaction mixture was heated to reflux for 5 h and cooled. The reaction mixture was diluted with ethyl acetate, washed with brine, dried over anhydrous sodium sulfate, filtered and concentrated. The crude product was purified by silica gel column chromatography (methylene chloride/methanol, 95/5) to 0.45 g (38%) of a white foam. The free base (0.23 g, 0.59 mmol) was dissolved in ethyl acetate, and precipitated with one equivalent of HCl in ether to give the title compound (0.16 g, 62%) as monohydrochloride, 1.0 hydrate: mp 215° C. (dec.); $^1$H NMR (DMSO, 400 MHz), 1.52–1.59 (m, 2H), 1.81–1.84 (m, 3H), 2.61 (d, 2H), 3.02–3.08 (m, 2H), 3.25–3.30 (m, 6H), 4.46 (t, 2H), 6.44–7.33 (m, 9H), 10.25 (br s, 1H), 10.98 (br s, 1H), 11.14 (br s, 1H); MS (FAB) m/z 392 (M+H)$^+$.

Elemental Analysis Calcd for C$_{24}$H$_{26}$FN$_2$O.HCl.H$_2$O

Theory: C, 64.64; H, 6.55; N, 9.42.

Found: C, 64.76; H, 6.40.; N, 9.08.

EXAMPLE 2

5-Fluoro-3-[[1-[2-(1H-indol-4-yloxy)propyl]-4-piperidinyl]methyl]-1H-indole

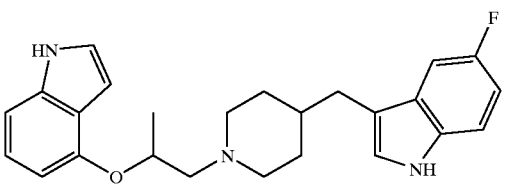

To a solution of 5-fluoro-3-[(4-piperidinyl)methyl]-1H-indole (0.25 g, 1.1 mmol) in DMSO (15 mL) containing triethylamine (0.11 g, 1.3 mmol) was added 2-methyl-2-(1H-indol-4-yloxy)-chloroethane (0.3 g, 1.2 mmol). The reaction mixture was heated to 80° C. for 18 h and cooled. The reaction mixture was poured into water (100 mL), and extracted with methylene chloride. The organic layer was washed with water and dried over anhydrous sodium sulfate, filtered, and the solvent evaporated. Chromatography (6% methanol-methylene chloride containing 1% ammonium hydroxide) afforded 72 mg (18%) of a yellow foam. The hydrochloride salt was prepared by adding an excess 1 M HCl in ether to a solution of the free base in ethanol: mp 130–132° C.; MS (EI) m/z 406 (M+).

Elemental Analysis Calcd for C$_{25}$H$_{28}$FN$_3$O.HCl. 1.5H$_2$O

Theory: C, 64.02; H, 6.88; N, 8.96.

Found: C, 64.34; H, 6.52.; N, 8.65.

The results of the tests with compounds representative of this invention are given in the immediately following table.

| Example No. | Ki (nM) Serotonin Transporter [3H]paroxetine | Ki (nM) 5-HT1A [3H]DPAT |
|---|---|---|
| 1 | 0.08 | 47 |
| 2 | 0.59 | 14% @ 100 nM |

The compounds of this invention are useful in methods for the treatment of depression as well as other serotonin-related disorders including, but not limited to, anxiety, generalized anxiety disorder, panic disorder, obsessive-compulsive disorder, sleep disorders, sexual dysfunction, bipolar disorders, psychosis, stress-related disorders, including post-traumatic stress disorders, Tourettes' syndrome, attention deficit disorder, with and without hyperactivity, alcohol and drug addiction, Alzheimer's disease, Parkinson's disease, obesity and acute and chronic pain, including migraine pain. Chemical dependencies and addictions which may be treated with compounds of this invention include those to opiates, benzodiazepines, cocaine, nicotine and ethanol.

The compounds herein are also useful in methods of enhancing cognition in a mammal, preferably a human, particularly in a mammal experiencing a cognitive deficit as a result of or in association with Alzheimer's disease or Parkinson's disease.

Each of these methods of treatment comprise administering a pharmaceutically effective amount of a compound of this invention, or a pharmaceutically acceptable salt thereof, to a mammal in need of such treatment or enhancement. A pharmaceutically or therapeutically effective amount of the compounds herein is understood to comprise an amount of the compound(s) in question which will obtain at least a minimum of desired effect in preventing, treating, inhibiting or managing the symptoms or causes of the malady in question. More preferably, the amount will be the minimum needed to alleviate or remove the undesirable physiological consequences of the malady in question and inhibit or prevent their re-occurrence.

This invention also provides pharmaceutical formulations comprising a pharmaceutically or therapeutically effective amount of a compound of this invention, or a pharmaceutically acceptable salt thereof, and a pharmaceutically acceptable carrier or excipient.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

What is claimed:

1. A compound of the formula:

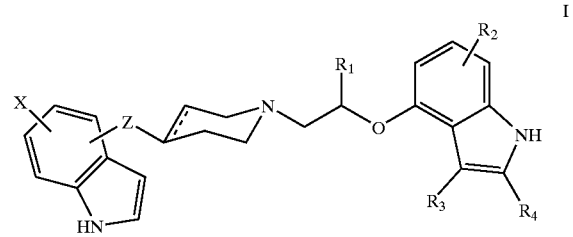

wherein;
$R_1$ is hydrogen or alkyl of from 1 to 6 carbon atoms;
$R_2$, $R_3$, and $R_4$ are each independently selected from hydrogen, alkyl of from 1 to 6 carbon atoms, or halogen;
X is selected from hydrogen, halogen, CN, or $C_1$–$C_6$ alkoxy;
Z is $(CH_2)_n$ or carbonyl;
n is 1 or 2; and
the dashed line indicates an optional double bond;
or a pharmaceutically acceptable salt thereof.

2. A compound of claim 1 of the formula:

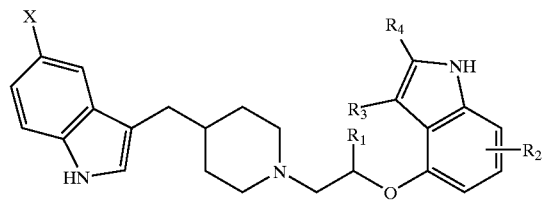

wherein:
X is selected from hydrogen, halogen, CN, or $C_1$–$C_6$ alkoxy;
$R_1$ is hydrogen or alkyl of from 1 to 3 carbon atoms; and
$R_2$, $R_3$, and $R_4$ are each independently selected from hydrogen, alkyl of from 1 to 6 carbon atoms, or halogen;
or a pharmaceutically acceptable salt thereof.

3. A compound of claim 1 of the formula:

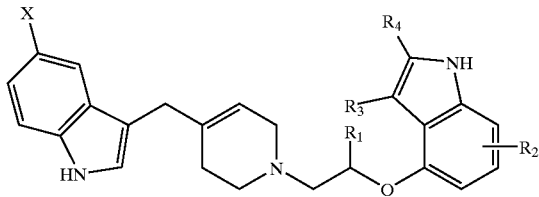

wherein:
   X is selected from hydrogen, halogen, CN, or $C_1$–$C_6$ alkoxy;
   $R_1$ is hydrogen or alkyl of from 1 to 3 carbon atoms; and
   $R_2$, $R_3$, and $R_4$ are each independently selected from hydrogen, alkyl of from 1 to 6 carbon atoms, or halogen;
or a pharmaceutically acceptable salt thereof.

4. A compound of claim 1 which is 5-Fluoro-3-{1-[2-(1H-indol-4-yloxy)ethyl]-piperidin-4-ylmethyl}-1H-indole, or a pharmaceutically acceptable salt thereof.

5. A compound of claim 1 which is 5-Fluoro-3-[[1-[2-(1H-indol-4-yloxy)propyl]-4-piperidinyl]methyl]-1H-indole, or a pharmaceutically acceptable salt thereof.

6. A pharmaceutical composition comprising a pharmaceutically effective amount of a compound of claim 1, or a pharmaceutically acceptable salt thereof, and a pharmaceutically acceptable carrier or excipient.

7. A pharmaceutical composition of claim 5 in which the compound of claim 1 is 5-Fluoro-3-{1-[2-(1H-indol-4-yloxy)ethyl]-piperidin-4-ylmethyl}-1H-indole, or a pharmaceutically acceptable salt thereof.

8. A pharmaceutical composition of claim 5 in which the compound of claim 1 is 5-Fluoro-3-[[1-[2-(1H-indol-4-yloxy)propyl]-4-piperidinyl]methyl]-1H-indole, or a pharmaceutically acceptable salt thereof.

9. A method of treating depression in a mammal, the method comprising administering to a mammal in need thereof a pharmaceutically effective amount of a compound of claim 1, or a pharmaceutically acceptable salt thereof.

10. A method of treating anxiety in a mammal, the method comprising administering to a mammal in need thereof a pharmaceutically effective amount of a compound of claim 1, or a pharmaceutically acceptable salt thereof.

* * * * *